US007014625B2

(12) United States Patent
Bengtsson

(10) Patent No.: US 7,014,625 B2
(45) Date of Patent: Mar. 21, 2006

(54) NEEDLE INSERTION DEVICE

(75) Inventor: Henrik Bengtsson, Frederiksberg (DK)

(73) Assignee: Novo Nordick A/S, Bagsvaud (DK)

( * ) Notice: Subject to any disclaimer, the term of this patent is extended or adjusted under 35 U.S.C. 154(b) by 203 days.

(21) Appl. No.: 10/679,631

(22) Filed: Oct. 6, 2003

(65) Prior Publication Data
US 2004/0116865 A1 Jun. 17, 2004

Related U.S. Application Data

(60) Provisional application No. 60/419,310, filed on Oct. 17, 2002.

(30) Foreign Application Priority Data
Oct. 7, 2002 (DK) .............................. 2002 01493

(51) Int. Cl.
*A61M 37/00* (2006.01)
(52) U.S. Cl. ..................................................... 604/131
(58) Field of Classification Search ................ 604/158, 604/142, 164, 145, 131, 147, 136, 153, 138, 604/156, 141, 157, 180
See application file for complete search history.

(56) References Cited

U.S. PATENT DOCUMENTS

| 1,934,046 A | * | 11/1933 | Demarchi ................... 604/115 |
| 2,605,765 A | | 8/1952 | Kollsman |
| 4,340,048 A | | 7/1982 | Eckenhoff ................... 128/213 |
| 4,552,561 A | | 11/1985 | Eckenhoff et al. .......... 604/896 |
| 5,390,671 A | | 2/1995 | Lord et al. ................... 128/635 |
| 5,391,950 A | | 2/1995 | Krawczak .................... 327/384 |
| 5,482,473 A | | 1/1996 | Lord et al. ..................... 439/67 |
| 5,527,288 A | * | 6/1996 | Gross et al. ................. 604/140 |
| 5,568,806 A | | 10/1996 | Cheney, II et al. ......... 128/635 |
| 5,616,132 A | | 4/1997 | Newman ..................... 604/185 |
| 5,814,020 A | | 9/1998 | Gross .......................... 604/41 |
| 5,820,622 A | | 10/1998 | Gross et al. ............. 604/890.1 |
| 5,858,001 A | | 1/1999 | Tsals et al. ................. 604/135 |
| 5,931,814 A | * | 8/1999 | Alex et al. ................... 604/131 |

(Continued)

FOREIGN PATENT DOCUMENTS

EP 1 177 802 A1 2/2002

(Continued)

*Primary Examiner*—Manuel Mendez
(74) *Attorney, Agent, or Firm*—Marc A. Began, Esq.; Reza Green, Esq.; Richard W. Bork, Esq.

(57) ABSTRACT

The invention relates to a needle insertion device comprising a housing with a mounting surface adapted for application to the skin of a subject, where the mounting surface defines a general plane and has a needle aperture formed therein. Adhesive means is arranged on the mounting surface for adhering the insertion device to the skin of the subject, the adhesive means surrounding the needle aperture. A needle comprises a distal pointed end adapted to penetrate the skin of the subject, the pointed end being arranged within the housing in respect of the general plane. The mounting surface surrounding the needle aperture is moveable between a first position in which the pointed end of the needle is arranged within the housing, and a second position in which the pointed end of the needle projects through the needle aperture, thereby pulling the skin portion corresponding to the intended site of needle insertion against the needle.

16 Claims, 3 Drawing Sheets

U.S. PATENT DOCUMENTS

| | | | |
|---|---|---|---|
| 5,951,493 A * | 9/1999 | Douglas et al. | 600/583 |
| 5,954,643 A | 9/1999 | VanAntwerp et al. | 600/316 |
| 5,957,895 A | 9/1999 | Sage et al. | 604/181 |
| 6,280,148 B1 | 8/2001 | Zengerle et al. | 417/44.1 |
| 6,896,666 B1 * | 5/2005 | Kochamba | 604/141 |
| 2002/0022798 A1 | 2/2002 | Connelly et al. | 604/93.01 |

FOREIGN PATENT DOCUMENTS

| | | |
|---|---|---|
| GB | 1011301 | 11/1965 |
| WO | 95/13838 | 5/1995 |
| WO | 02/15965 A2 | 2/2002 |
| WO | 02/40083 | 5/2002 |

* cited by examiner

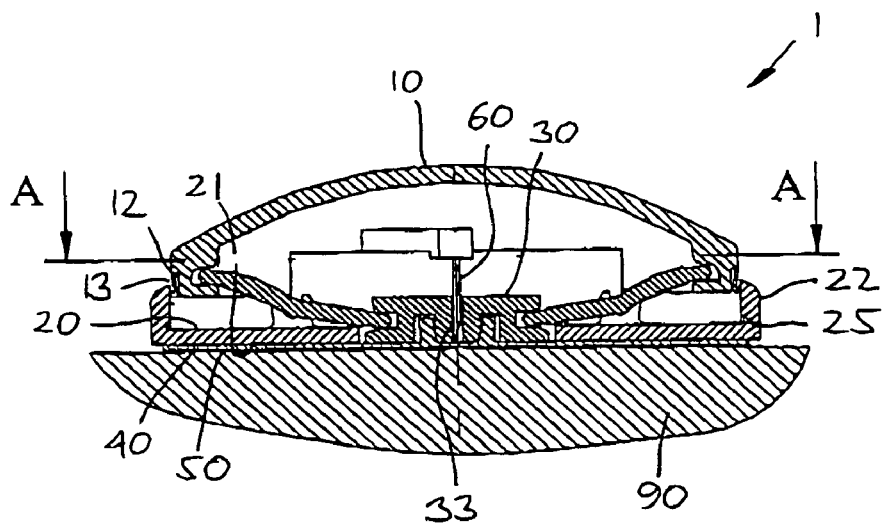
Fig. 1
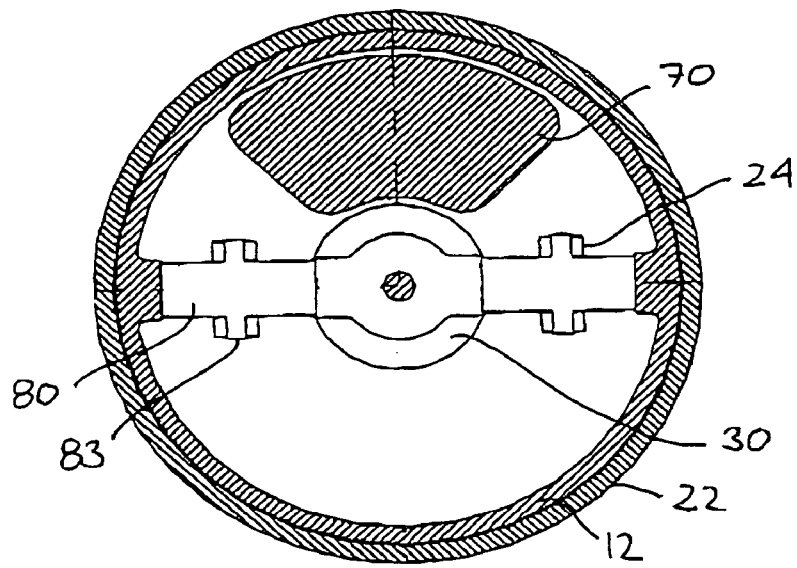
Fig. 2  A-A
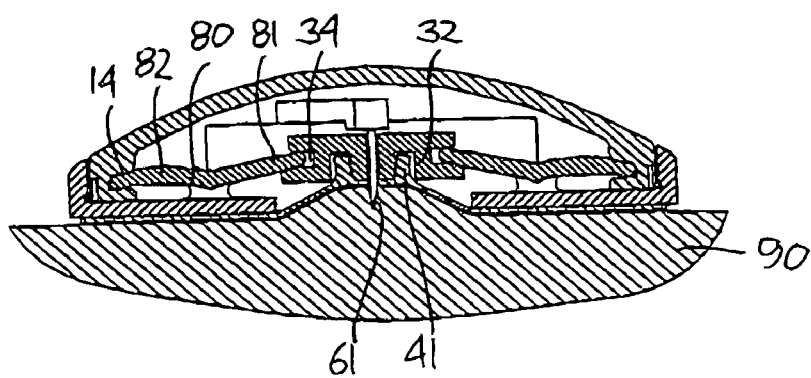
Fig. 3 ary use
NEEDLE INSERTION DEVICE

CROSS REFERENCE TO RELATED APPLICATIONS

This application claims priority under 35 U.S.C. 119 of Danish application no. PA 2002 01493 filed Oct. 7, 2002 and U.S. provisional application No. 60/419,310 filed Oct. 17, 2002, the contents of both are fully incorporated herein by reference.

The present invention generally relates to the insertion of needles or needle-like members. More specifically, the invention relates to a needle device for placing a needle transcutaneously at a selected site within the body of a patient and having a contact surface for attaching the device to a patient's skin. Especially, the invention relates to insertion of an infusion needle for the infusion of a drug, to insertion of a needle-formed sensor, as well as to insertion of an insertion needles for easy transcutaneous placement of a transcutaneous device such as a sensor.

BACKGROUND OF THE INVENTION

In the disclosure of the present invention reference is mostly made to the treatment of diabetes by injection or infusion of insulin, however, this is only an exemplary use of the present invention.

Portable drug delivery devices for delivering a drug to a patient are well known and generally comprise a reservoir adapted to contain a liquid drug and having an outlet in fluid communication with a hollow infusion needle, as well as expelling means for expelling a drug out of the reservoir and through the skin of the subject via the hollow needle. Such devices are often termed infusion pumps.

Basically, infusion pumps can be divided into two classes. The first class comprises durable infusion pumps which are relatively expensive pumps intended for 3–4 years use, for which reason the initial cost for such a pump often is a barrier to this type of therapy. Although more complex than traditional syringes and pens, the pump offer the advantages of continuous infusion of insulin, precision in dosing and optionally programmable delivery profiles and user actuated bolus infusions in connections with meals.

Addressing the above problem, several attempts have been made to provide a second class of drug infusion devices that are low in cost and convenient to use. Some of these devices are intended to be partially or entirely disposable and may provide many of the advantages associated with an infusion pump without the attendant cost and inconveniencies, e.g. the pump may be prefilled thus avoiding the need for filling or refilling a drug reservoir.

The disposable pumps generally comprises a skin-contacting mounting surface adapted for application to the skin of a subject by adhesive means, and with the infusion needle arranged such that in a situation of use it projects from the mounting surface to thereby penetrate the skin of the user, whereby the place where the needle penetrates the skin is covered while the appliance is in use.

The infusion needle may be arranged to permanently project from the mounting surface such that the needle is inserted simultaneously with the application of the infusion pump. Examples of this configuration can be found in U.S. Pat. Nos. 2,605,765, 4,340,048 and in EP 1 177 802. Although this configuration provides a simple and cost-effective solution, it has a number of drawbacks. For example, the actual user-performed piercing of the tissue with the needle is often problematic as people who are not experts in medicine are usually insufficiently practised to place such a needle correctly and they often suffer from a fear of the likely pain. Further, the permanently projecting needle increases the risk for accidental needle injuries.

Addressing the above problems, infusion pump devices have been proposed in which the pump device is supplied to the user with the needle in a retracted state, i.e. with the distal pointed end of the needle "hidden" inside the pump device, this allowing the user to place the pump device on the skin without the possibility of observing the needle. When first the needle is hidden, at least some of the fear is overcome making the introduction of the needle in a second step less problematic. To further reduce the fear and pain associated with the introduction of the needle, many recent pump devices have been provided with actuatable needle insertion means, which just has to be released by the user after which e.g. spring means quickly will advance the needle through the skin.

For example, U.S. Pat. No. 5,957,895 discloses a liquid drug delivery device comprising a bent injection needle which is adapted to project through a needle aperture in the bottom surface of the housing in a situation of use. A movable needle carrier is disposed in the housing for carrying the injection needle and for causing the injection end of the needle to project through the needle aperture upon movement of the needle carrier.

U.S. Pat. No. 5,931,814 discloses an infusion device having a housing with a drug reservoir, an infusion needle (or cannula) communicating with the reservoir, means for inserting the needle, and pump means for discharging the reservoir contents through the needle. The needle is fixed relative to the housing and projects beyond the lower skin-contacting surface of the housing to the depth required for injection. The needle is surrounded by a protective element which is moved by spring means from a first end position in which the protective device projects beyond the lower surface of the housing and beyond the needle to a second end position in which the protective device does not project beyond the underside of the casing. An advantage of this design is that the needle is arranged in a fixed position relative to the reservoir. Before the device is taken off the patient, the protective element can be extended into its initial position for protecting the needle. WO 02/15965 discloses a similar infusion device in which a base plate member acts as a protecting element until an upper part of the device, to which the needle is fixed, is moved down into engagement with the base plate member.

Although in the known devices it may be possible to withdraw either the needle into the housing after use or extending a protecting element to cover the needle, this operation may not necessarily be performed when the device is removed from the skin of the user, this resulting in the used infusion needle projecting from the lower surface of the device. The same situation prevails in case the device is operated incorrectly by the user such that the needle is forwarded or the protecting element is withdrawn prior to the mounting operation. Correspondingly, it would be desirable if an infusion device could be provided which reduces the risk of accidental needle sticks from projecting used infusion needles.

Before turning to the disclosure of the present invention, a different type of device relying on the insertion of a needle or needle-like structure will be described.

Although drug infusion pumps, either disposable or durable, may provide convenience of use and improved treatment control, it has long been an object to provide a drug infusion system for the treatment of e.g. diabetes which would rely on closed loop control, i.e. being more or less fully automatic, such a system being based on the measurement of a value indicative of the condition treated, e.g. the blood glucose level in case of insulin treatment of diabetes.

A given monitor system for measuring the concentration of a given substance may be based on invasive or non-invasive measuring principles. An example of the latter would be a non-invasive glucose monitor arranged on the skin surface of a patient and using near-IR spectroscopy, however, the present invention is concerned with the introduction of a transcutaneous device such as a needle-formed sensor element.

The sensor may be placed subcutaneously being connected to external equipment by wiring or the substance (fluid) to be analysed may be transported to an external sensor element, both arrangements requiring the placement of a subcutaneous component, the present invention addressing both arrangements. However, for simplicity the term "sensor" is used in the following for both types of sensor elements.

Turning to the sensor elements per se, relatively small and flexible electrochemical sensors have been developed for subcutaneous placement of sensor electrodes in direct contact with patient blood or other extra-cellular fluid (see for example U.S. Pat. No. 5,482,473), wherein such sensors can be used to obtain periodic or continuous readings over a period of time. Insertion devices for this type of sensors are described in, among others, U.S. Pat. Nos. 5,390,671, 5,391, 950, 5,568,806 and 5,954,643 which hereby are incorporated by reference.

More specifically, U.S. Pat. No. 5,954,643 discloses an insertion set comprising a mounting base supporting a proximal end of a flexible thin film sensor, the sensor including a distal segment with sensor electrodes thereon which protrudes from the mounting base for transcutaneous placement, wherein the sensor distal segment is slidably carried by a slotted insertion needle fitted through the assembled base. Placement of the insertion set against the patient's skin causes the insertion needle to pierce the skin to carry the sensor electrodes to the desired subcutaneous site, after which the insertion needle can be slidably withdrawn from the insertion set. A similar arrangement is known from U.S. Pat. No. 5,568,806.

Although the insertion needle normally is removed before the insertion set, it would be desirable if contact with the sensor element could be prevented.

DISCLOSURE OF THE INVENTION

Having regard to the above-identified problems, it is an object of the present invention to provide a skin-mountable needle insertion device which reduces the likelihood that a user comes into contact with an infusion needle or any other transcutaneously insertable structure prior to use or when the device is removed from the skin of the user after a period of use.

The present invention is based on the concept that the risk of accidental contact with a needle or similar structure can be reduced if the needle as such is arranged inside the device, i.e. the distal pointed end is arranged such that it does not protrude from the lower skin-contacting surface as defined by the general plane of that surface. As the needle does not protrude from the lower surface, normally no insertion would take place when the device is mounted onto the skin of the user, however, corresponding to the present invention, the skin portion corresponding to the intended site of needle insertion is pulled up against the needle by adhesive means.

More specifically, in a first aspect a needle insertion device is provided comprising a housing with a mounting surface adapted for application to the skin of a subject (e.g. user or patient), where the mounting surface comprises a first portion being fixed relative to the housing, the first portion defining a general plane, and a second portion having a needle aperture (33) formed therein. Adhesive means is arranged on the first and second portions of the mounting surface for attaching the insertion device to the skin of the subject. A needle comprises a distal pointed end adapted to penetrate the skin of the subject. The second portion is moveable between a first position in which the pointed end of the needle is arranged within the housing relative to the second portion, and a second position in which the pointed end of the needle projects through the needle aperture, thereby pulling the skin portion corresponding to the intended site of needle insertion against the needle. As the pulled-in skin portion is elastic, the device is configured to be locked corresponding to the second position of the moveable surface portion, e.g. by mechanical locking means or by a bi-stable member. The length of the projecting portion of the needle and thereby the depth of penetration may be from 0.5 to about 8 mm, preferably about 3–5 mm. In the context of the present application the term "needle" also encompasses an array of micro needles, i.e. a plurality of very short needles mounted together and acting as a single "needle means". The adhesive means may be in the form of a pressure-sensitive adhesive provided with a peelable protection liner.

In the present context the term "needle" is used to denote any structure having an oblong, needle-like appearance, e.g. infusion needle, needle sensor or insertion needle.

The adhesive means surrounding the needle aperture should be arranged in such close proximity to the needle aperture (and thereby the needle in a situation of use) that it is ensured that the needle penetrates the skin, i.e. in case the distance was too large the needle may depress the skin surface without actually penetrating the skin. Correspondingly, the adhesive means may be arranged circumferentially at a distance of less than 5 mm, preferably less than 3 mm, more preferably less than 2 mm and most preferably less than 1 mm from the aperture. In case the opening in the adhesive means is substantially circular, these values would represent a radius.

The term "general plane" is used to describe the overall configuration of the mounting surface in its initial state which for example may be planar or slightly inwardly or outwardly curved relative to the housing. In a functional aspect, the general plane may correspond to a planar surface on which the device is placed with the second portion of the mounting surface in its retracted second position.

The second moveable portion of the mounting surface may be arranged on an edge portion of the mounting surface or the second portion may be arranged fully surrounded by the first portion. Advantageously, the needle is non-displaceable relative to the first portion of the mounting surface.

To move the aperture portion between the first and the second position, user operatable actuating means is advantageously incorporated. The actuating means may be adapted for also moving the aperture portion between the second and the first position.

In a further exemplary embodiment, the housing comprises a base portion providing the first portion of the mounting surface, an actuating member, and an aperture member providing the second portion of the mounting surface. The actuating member is moveable relative to the first portion between a first and a second position, whereby the aperture member is moved between its first and second position. In an exemplary embodiment, the actuating member is adapted for also moving the aperture member between the second and the first position. The actuating member may have any desirable configuration, e.g. a traditional button, a ring-formed member or a larger portion of the housing, and may be actuated for example by a pushing or rotating action. Locking means may be provided between the actuating member and the housing. The actuation member may be associated with transmission means (e.g. mechanical) arranged between the actuating member and the aperture member for transmitting movement from the actuating member to the aperture member, or spring means released by the actuating member. The transmission means may comprise one or more bi-stable members having a first position corresponding to the first position of the aperture member, and a second position corresponding to the second position of the aperture member, this arrangement allowing the device to "snap" between the two positions and also provides a locking means for the two positions.

In an exemplary embodiment, the first and second portions of the mounting surface is arranged substantially in the same plane when the second portion is positioned in its first position, i.e. the device is provided in an initial state with a plane or slightly convex or concave lower surface.

To provide a continuous and sealed lower surface, an elastic sealing member may be arranged between the base portion and the moveable aperture member, the elastic member allowing the two surfaces to move relatively to each other. In an exemplary embodiment, an elastic surface member substantially covers the base portion and the aperture member to provide a common lower surface.

In a further exemplary embodiment, the needle insertion device comprises a bi-stable base member in which the needle aperture is arranged, the bi-stable member at least defining the second portion of the mounting surface, the bi-stable member having a first outwardly-curving position in which the pointed end of the needle is arranged within the housing relative to the second portion, and a second inwardly-curving position in which the pointed end of the needle projects through the needle aperture.

In order to further reduce the likelihood of needle injury, the mounting surface and the needle may be configured such that even when the needle projects through the needle aperture, the device can be arranged on a planar surface without the needle coming into contact with that surface.

As discussed above, the needle insertion device of the present invention is intended for use in combination with other structures to thereby form, for example, an infusion device or system or a sensor device or system. The additional structures providing these functions may be formed either integrally with the needle insertion device or the needle insertion device may be adapted to cooperate with external structures, the cooperation providing the desired functionality. As an example of the latter, the needle insertion device may be in the form of a so-called infusion set comprising means allowing it to be connected to a drug source, e.g. comprising a tubing with connector means adapted to be connected to a drug delivery device such as an infusion pump.

However, in a second aspect an infusion device is provided comprising an insertion device as described above, wherein the needle is a hollow infusion needle, the device further comprising a reservoir adapted to contain a liquid drug and comprising in a situation of use an outlet in fluid communication with the infusion needle. The infusion device may comprise expelling means for expelling a drug out of the reservoir and through the skin of the subject via the infusion needle, or it may be adapted to cooperate with such expelling means.

The infusion device may be intended to be partially or entirely disposable, it may be prefilled just as it may provide constant rate only infusion or also bolus infusions. The expelling means may be of any desirable nature, such as known from U.S. Pat. Nos. 4,340,048 and 4,552,561 (based on osmotic pumps), U.S. Pat. No. 5,858,001 (based on a piston pump), U.S. Pat. No. 6,280,148 (based on a membrane pump), U.S. Pat. No. 5,957,895 (based on a flow restrictor pump (also know as a bleeding hole pump)), or U.S. Pat. No. 5,527,288 (based on a gas generating pump), which all in the last decades have been proposed for use in inexpensive, primarily disposable drug infusion pumps.

In a third aspect the needle insertion device of the invention comprises a needle in the form of a needle sensor comprising sensor means capable of being influenced by a body substance and producing a signal corresponding to a parameter thereof, e.g. the blood glucose concentration. The needle sensor may comprise a pointed distal end and have a rigidity allowing it to be introduced without the aid of an insertion needle as a "general" needle as described above, however, it may be desirable to provide an insertion needle adapted to cooperate with the needle sensor for inserting the needle sensor subcutaneously. In this case the needle sensor may have a blunt distal end, the insertion needle comprising a pointed distal end in accordance with the invention.

Thus, in a further embodiment the needle is in the form of an insertion needle for inserting a transcutaneous device, e.g. a needle formed sensor comprising a distally arranged sensor element. The insertion needle may have any desirable configuration such as solid or grooved. The signal from the sensor element is conducted through the needle sensor to a control means adapted to receive the signals from the sensor element and generate signals in response thereto providing an indication of the desired body substance parameter, e.g. the glucose level which may be indicated on an associated display. The control means may be formed integrally with the needle device or the signals may be transmitted to an external control unit. In contrast to an infusion needle, an insertion needle will have to be withdrawn after the sensor has been placed transcutaneously, either into the device or fully removed therefrom. The same apply to the individual sensors, which after used should be withdrawn.

The sensor means may be also be arranged within the device and be adapted to draw a body substance through a hollow needle, the sensor producing a signal corresponding to a parameter of the body substance, e.g. the blood glucose concentration.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject.

BRIEF DESCRIPTION OF THE DRAWINGS

In the following the invention will be further described with references to the drawings, wherein FIG. 1 shows in a "vertical" cross-section a first embodiment of a needle insertion device in accordance with the invention, the device being in an initial state, FIG. 2 shows the device of FIG. 1 in a subsequent state, FIG. 3 shows a "horizontal" cross-sectional view along the line A—A in FIG. 1.

In the figures like structures are identified by like reference numerals.

DESCRIPTION OF EXEMPLARY EMBODIMENTS

Figure 4:
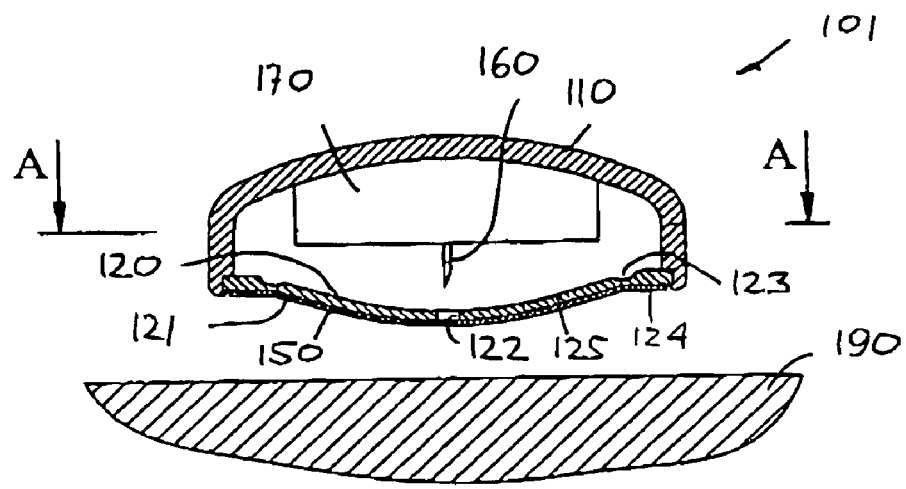
FIG. 4 shows in a "vertical" cross-section a second embodiment of a needle insertion device in accordance with the invention, the device being in an initial state.

When in the following terms as "upper" and "lower", "right" and "left", "horizontal" and "vertical" or similar relative expressions are used, these only refer to the appended figures and not to an actual situation of use.

FIGS. 1 and 3 show in vertical respectively horizontal section a schematic representation of a first embodiment of the invention. Correspondingly, the configuration of the different structures as well as there relative dimensions are intended to serve illustrative purposes only.

More specifically, an infusion device 1 comprises a housing having an upper member 10 a lower base plate member 20, and an aperture member 30, the three members in combination defining the general exterior configuration of the device.

The base plate member comprises a lower mounting surface 21 adapted for application towards the skin of a user, the mounting surface defining a general plane which in the shown embodiment is planar. The base plate member is provided with an upstanding peripheral flange portion 22 and a central opening 23 in which the aperture member 30 is arranged. On the upper side the base plate member is provided with a pair of axle gripping means 24 (to be described in greater detail below). The aperture member comprises a lower surface 31 with a lower groove 32, an axially arranged needle aperture 33 and first groove means 34 arranged on the circumference. The infusion device further comprises an elastic membrane member 40 having an upper surface and a lower surface. The upper surface is attached to the lower surfaces of the base plate member and the aperture member substantially covering both members thereby providing a common lower surface. The elastic member may be provided with a central needle aperture arranged in alignment with the needle aperture in the aperture member, however, in the shown embodiment the elastic membrane is adapted to be penetrated by the needle. The membrane member also comprises a flange member 41 on the upper surface which engages the lower groove 32 of the aperture member to thereby securely hold the two members in engagement with each other. In order to adhere the device to the patient's skin, the lower surface of the elastic member is provided with an adhesive layer 50.

The upper member comprises an upwardly curved central portion 11 and a circumferential downwardly projecting rim portion 12, the rim portion comprising an outer surface provided with gripping means 13 adapted to engage corresponding gripping means 25 arranged on the inner surface of the base plate flange portion 22, and an inner surface comprising second groove means 14. The device further comprises a pair of transmission members 80, each member having an inner end portion 81, an outer end portion 82 and a central portion with a pair of laterally projecting axle members 83. The axle members are mounted in the axle gripping means 24 providing a pivoting connection between the transmission members and the base plate member. Further, the inner and outer end portions 81, 82 are arranged pivotally in the first respectively the second groove means 34, 14, this arrangement providing a mechanical connection between the upper member, the base plate member and the aperture member via the two transmission members, this connection in combination with the cooperating flange and rim portions allowing the members to move relative to each other in a controlled and restricted manner as will be explained in greater detail below.

Arranged in the interior of the housing and fixedly connected to the base plate member, the infusion means is provided, i.e. a reservoir adapted to contain a liquid drug and comprising an outlet in fluid communication with an infusion needle 60, as well as expelling means for expelling a drug out of the reservoir and through the skin of the subject via the infusion needle. As the specific nature of the reservoir and the expelling means is not important for the understanding of the present invention, these components are merely shown schematically as a common infusion member 70. The infusion needle 60 comprising a proximal end in fluid communication with the reservoir and a distal pointed end 61 is arranged centrally in the housing and coaxially with the needle aperture in the aperture member, thereby allowing the latter to move axially relative to the needle. As appears, the distal end of the needle is arranged just above the general plane defined by the lower mounting surface of the base plate member.

Next, with reference to FIGS. 1 and 2, use of the above-described first embodiment will be described. The infusion device 1 is supplied in an initial configuration with a release liner covering the adhesive layer. After removing the liner the user grips the device on the peripheral flange portion 22 and places the device on a skin portion 90, this as shown in FIG. 1. As appears, both the base plate member 20 and the aperture member 30 are attached to the skin portion via the adhesive layer 50 and the membrane member 40. Thereafter the user displaces the upper housing member downwardly until the cooperating gripping means 13 of the rim portion engages the corresponding gripping means 25 arranged on the inner surface of the base plate flange portion 22. Simultaneously with this action, the outer portions of the pivoting transmission members 80 are displaced downwardly whereby the inner portions thereof are displaced upwardly, thereby moving the aperture member from a first position in which the pointed end of the needle is arranged within the needle aperture 33 upwardly to a second position in which the pointed end of the needle projects through the needle aperture. As the skin of the user via the membrane member is adhered to the aperture member, this action results in the needle being introduced subcutaneously into the skin of the user, this as shown in FIG. 2. As the membrane member is attached to the aperture member only at the central portion thereof (by means of the flange member 41 which engages the lower groove 32 of the aperture member), the membrane is capable of bridging the height difference between the surrounding portion of the base member and the central aperture portion of the aperture member, thereby providing a smooth upwardly curved surface which will not disengage from the skin.

After use the infusion device may be removed in different ways in accordance with the actual design of the actuation means. In a simple embodiment (as shown) the upper housing member is permanently locked to the base plate member. Correspondingly, when the device is removed from the skin of the user, the needle will protrude from the lower surface, however, as the pointed distal end of the needle is arranged recessed in the mounting surface, the likelihood of injuries from the needle is reduced compared to devices in which the needle is not recessed. In the shown embodiment the needle is arranged above the lowest portion of the lower mounting surface 21 which means that even when the needle is protruding the device can be placed on a planar surface without the needle coming into contact with that surface. However, the locking means between the upper housing member and the base plate member may also be releasable, such that prior to removal of the device, the device can be brought back to the initial configuration with the needle protected in the needle aperture. To help move the aperture member back from its second to its first position, spring means may be provided biasing the aperture member (and the upper housing member) towards the initial position. The spring means may be in the form of additional spring members or the transmission members 80 may be configured as spring members being bent when the upper housing is depressed. The transmission members may also be in the form of a bi-staple member as will be described below with reference to FIGS. 4 and 5.

Figure 5:
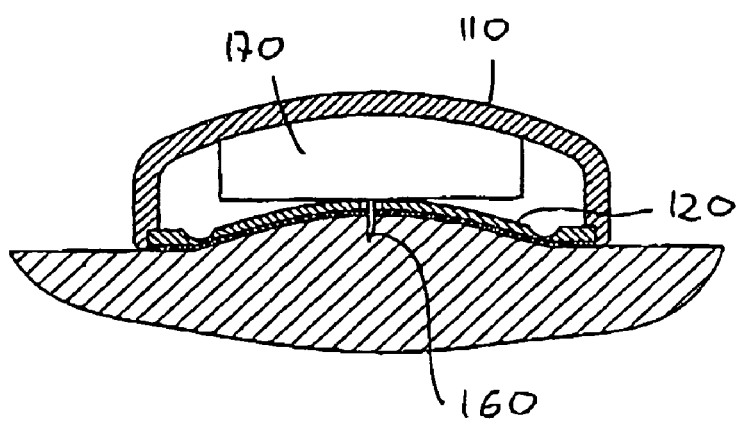
FIG. 5 shows the device of FIG. 4 in a subsequent state.

FIGS. 4 and 5 show a second embodiment. Instead of the three actuating members used in the first embodiment (i.e. the upper housing member, the transmission members and the aperture member), the actuating means in the second embodiment is formed integrally with a base plate member which provides the lower mounting surface as well as the means for moving the mounting surface surrounding the needle aperture between its first and second position.

More specifically, the infusion device 101 comprises a housing having an upper member 110 and a lower base plate member 120, the two members in combination defining the general exterior configuration of the device.

The base plate member comprises a lower mounting surface 121 adapted for application towards the skin of a user, the mounting surface defining a general convex plane. The base plate member is in the form of a circular bi-staple disc member provided with a central aperture 122 and is attached to the upper member at the periphery thereof. The bi-staple disc member comprises an outer non-moveable peripheral portion 124 attached to the housing, and a moveable inner portion 125 having a first outwardly-curving position (relative to the housing) in which the pointed end of an infusion needle is arranged within the housing (see FIG. 4), and a second inwardly-curving position in which the pointed end of the needle projects through the needle aperture (see FIG. 5). The disc will flex between the two positions corresponding to a circumferential groove 123 formed in the upper surface of the disc between the first and second portions. In order to mount the device on a patient's skin, the lower surface of the bi-staple member is provided with an adhesive layer 150. As appears, in contrast to the embodiment of FIG. 1 occupies the moveable portion of the mounting surface a relatively large proportion of the aggregate mounting surface, however, taken to the extreme the entire base plate member may be arranged to flex, whereby the outer non-moveable potion would be reduced to merely a "virtual" second portion defining the general plane.

Arranged in the interior of the housing and fixedly connected to the upper housing member, the infusion means is provided (in the figures shown as a common infusion member 170 corresponding to the infusion member 70 of the first embodiment). The associated infusion needle 160 comprises a proximal end in fluid communication with the reservoir and a distal pointed end 161 arranged centrally in the housing and coaxially with the needle aperture in the disc member, thereby allowing the latter to move axially relative to the needle. As appears, the distal end of the needle is arranged above the general plane defined by the lower mounting surface of the base plate member.

Next, with reference to FIGS. 4 and 5, use of the above-described second embodiment will be described. The infusion device 101 is supplied in an initial configuration with a release liner covering the adhesive layer. After removing the liner (as shown in FIG. 1), the user grips the device on the peripheral portion of the upper member and gently adheres the central aperture portion of the base plate member to the skin 190. As more pressure is applied to the device, the downwardly curved lower surface will be forced against the skin, however, at a given time the pressure on the central portion of the bi-staple disc member will overcome the necessary transition force, and the disc will swiftly flex upwardly to its second position in a snap action-like manner, pulling the skin towards the needle, whereby the needle is introduced subcutaneously into the skin of the user, this as shown in FIG. 5.

After use the infusion device is removed by simply pulling it off the skin. When the properties of the bi-staple member and the adhesive means are chosen properly, the disc member will be pulled downwardly and thereby flex to its first downwardly curving position before the skin will disengage from the skin of the user. By this arrangement, the infusion device will almost inevitably return to its initial position as shown in FIG. 4, thereby reducing the likelihood of injuries from the needle. To further improve safety, the infusion device may be provided with locking means (not shown) by which the device can be locked with the disc member in its first position, this protecting against needle injuries before as well as after use of the device. However, as was the case for the first embodiment, the needle is arranged above the lowest portion of the lower mounting surface 121 (which is the peripheral portion) when this is in its upper position, which means that even when the needle is protruding the device can be placed on a planar surface without the needle coming into contact with that surface.

Figure 6:
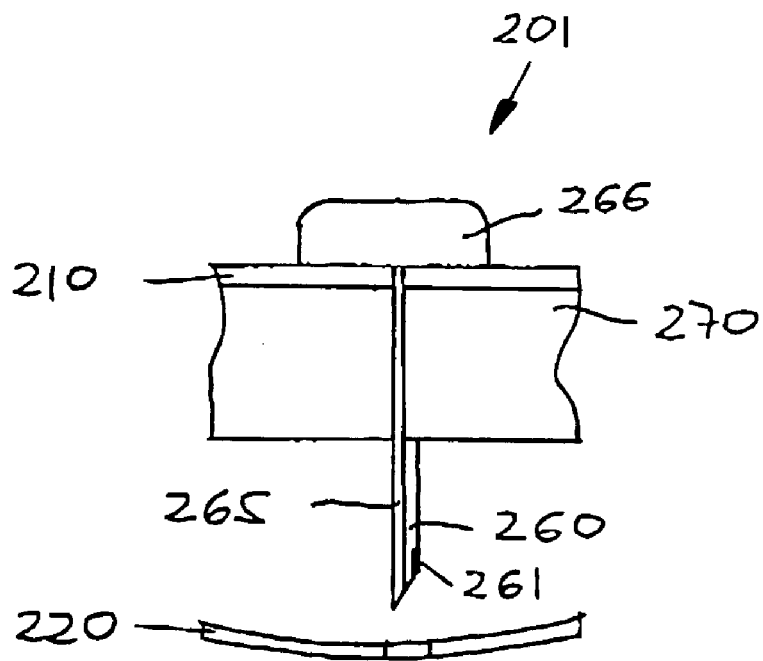
FIG. 6 shows in part a "vertical" cross-section a third embodiment of a needle insertion device in accordance with the invention, the device being in an initial state.
Figure 7:
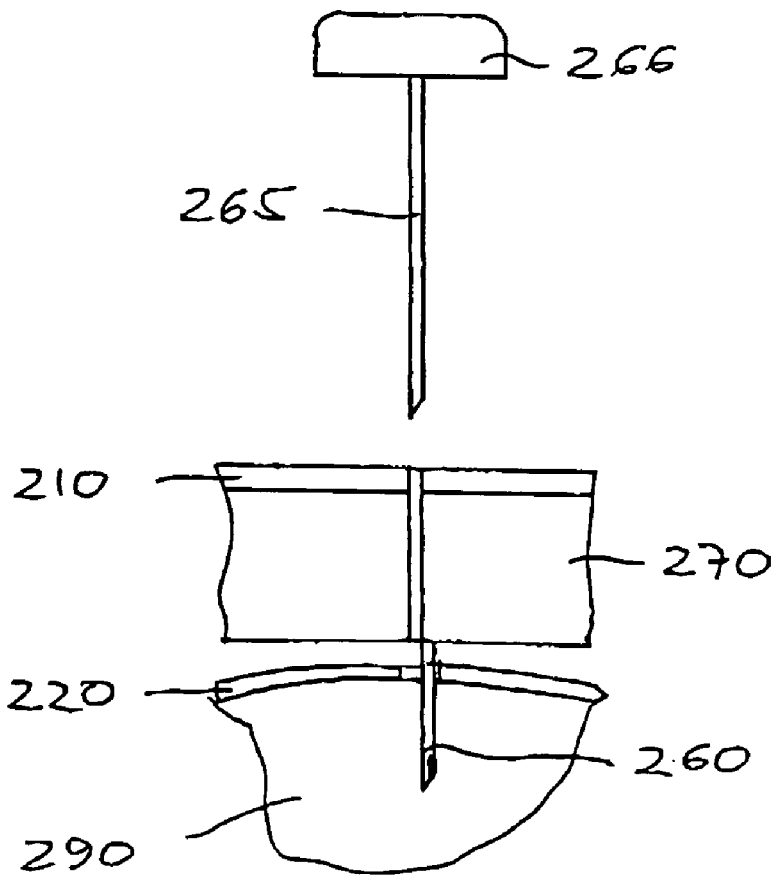
FIG. 7 shows the device of FIG. 6 in a subsequent state.

With reference to FIGS. 1–5 embodiments of the invention has been described in which the needle insertion device of the invention has been incorporated into an infusion device, however, with reference to FIGS. 6 and 7 a third embodiment will be described in which the needle insertion device of the invention has been incorporated into a sensor device 201.

The third embodiment has the same general configuration as the second embodiment comprising an upper member 210 and a lower base plate member 220, however, instead of an infusion needle, a needle-formed sensor member 260 is provided comprising a distal sensor element (261) capable of being influenced by a body substance and producing a signal corresponding thereto. The signal from the sensor element is conducted through the needle sensor to a control means 270 adapted to receive the signals from the sensor element and generate signals in response thereto providing an indication of the desired body substance parameter, e.g.

the glucose level which may be indicated on an associated display. The control means may be formed integrally with the sensor device (as shown) or the signals may be transmitted to an external control unit.

As the sensor member is relatively soft and flexible, an insertion needle 265 is provided to support the sensor during insertion. In contrast to an infusion needle, the insertion needle will have to be withdrawn after the sensor has been places subcutaneously, either into the device or fully removed therefrom. As the insertion needle provides the pointed distal end of the combined insertion needle and sensor member, it will normally be necessary to releasably lock the insertion needle during insertion, e.g. by providing locking means between a gripping portion 266 and the housing.

In use the third embodiment is used substantially in the same way as the second embodiment, the only difference being that the insertion needle is unlocked and withdrawn from the insertion device after application to the skin 290 of the user.

In the above description of the exemplary embodiments, the different structures providing mechanical and electrical contact and communication between the different components just as the means providing the described functionality for the different components (e.g. expelling means, reservoir, energy source, control means, display etc.) have been described to a degree to which the concept of the present invention will be apparent to the skilled reader. The detailed construction and specification for the different structures are considered the object of a normal design procedure performed by the skilled person along the lines set out in the present specification.

What is claimed is:

1. A needle insertion device comprising:
   (a) a housing, a mounting surface adapted for application to the skin of a subject, the mounting surface comprising a first portion being fixed relative to the housing, the first portion defining a general plane, and a second portion having a needle aperture formed therein,
   (b) adhesive means arranged on the first portion of the mounting surface for adhering the insertion device to the skin of the subject,
   (c) adhesive means arranged on the second portion of the mounting surface for adhering the insertion device to the skin of the subject,
   (d) a needle comprising a distal pointed end adapted to penetrate the skin of the subject,
   (e) wherein the second portion is moveable between a first position in which the pointed end of the needle is arranged within the housing relative to the second portion, and a second position in which the pointed end of the needle projects through the needle aperture.

2. A needle insertion device as defined in claim 1, wherein the first portion surrounds the second portion.

3. A needle insertion device as defined in claim 2, further comprising actuating means for moving the second portion between the first and the second position.

4. A needle insertion device as defined in claim 3, wherein the actuating means is adapted for also moving the first portion between the second and the first position.

5. A needle insertion device as defined in claim 3, comprising a base portion providing the first portion of the mounting surface, an actuating member, and an aperture member providing the second portion of the mounting surface, the actuating member being moveable relative to the base portion between a first and a second position, whereby the aperture member is moved between its first and second position.

6. A needle insertion device as defined in claim 5, wherein the actuating member is adapted for also moving the aperture member between the second and the first position.

7. A needle insertion device as defined in claim 5, further comprising transmission means arranged between the actuating member and the aperture member for transmitting movement from the actuating member to the aperture member.

8. A needle insertion device as defined in claim 7, wherein the transmission means comprises a bi-stable member having a first position corresponding to the first position of the aperture member, and a second position corresponding to the second position of the aperture member.

9. A needle insertion device as defined in claim 5, further comprising an elastic surface member bridging the transition between the base portion and the moveable aperture member.

10. A needle insertion device as defined in claim 9, wherein the elastic surface member substantially covers the base portion and the aperture member to provide a common surface.

11. A needle insertion device as defined in claim 2, wherein the first and second portions of the mounting surface are arranged substantially in the same plane when the first portion is positioned in its first position.

12. A needle insertion device as defined in claims 2, wherein the needle is non-displaceable relative to the first portion of the mounting surface.

13. A needle insertion device as defined in claim 1, comprising a bi-stable base member in which the needle aperture is arranged, the bi-stable member at least defining the second portion of the mounting surface, and having a first outwardly-curving position in which the pointed end of the needle is arranged within the housing relative to the second portion, and a second inwardly-curving position in which the pointed end of the needle projects through the needle aperture.

14. A needle insertion device as defined in claim 1, wherein the needle is a hollow infusion needle, the device further comprising:
   a reservoir adapted to contain a liquid drug and comprising in a situation of use an outlet in fluid communication with the infusion needle, and, preferably,
   expelling means for expelling a drug out of the reservoir and through the skin of the subject via the common fluid conduit means and a hollow needle.

15. A needle device as defined in claim 1, wherein the needle is in the form of a needle sensor comprising sensor means capable of being influenced by a body substance and producing a signal corresponding thereto.

16. A needle device as defined in claim 15, further comprising an insertion needle adapted to cooperate with a corresponding needle sensor for inserting the needle sensor subcutaneously.

* * * * *